(12) United States Patent
Manhes

(10) Patent No.: US 6,428,511 B2
(45) Date of Patent: Aug. 6, 2002

(54) TROCAR SPIKE WITH A POINT

(75) Inventor: Hubert Manhes, Vichy (FR)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/171,543

(22) PCT Filed: Apr. 25, 1997

(86) PCT No.: PCT/DE97/00838

§ 371 (c)(1),
(2), (4) Date: Sep. 3, 1999

(87) PCT Pub. No.: WO97/40758

PCT Pub. Date: Nov. 6, 1997

(30) Foreign Application Priority Data

Apr. 25, 1996 (DE) .......................................... 196 16 609

(51) Int. Cl.[7] .............................................. A61M 5/178
(52) U.S. Cl. ..................... 604/164.06; 606/170; 604/26
(58) Field of Search .......................... 604/26, 164, 166, 604/170, 173, 264, 272, 274, 23, 164.01, 164.06, 164.11, 164.12, 170.01, 170.02, 266, 268, 158; 606/185, 108, 167, 170; 600/433–435, 564, 567

(56) References Cited

U.S. PATENT DOCUMENTS 5,407,427 A * 9/1997 Zhu et al.
5,669,883 A * 9/1997 Scarfone et al.

* cited by examiner

Primary Examiner—Brian L. Casler
Assistant Examiner—LoAn H. Thanh
(74) Attorney, Agent, or Firm—St. Onge Steward Johnston & Reens LLC

(57) ABSTRACT

A trocar mandrel has a tip permitting the piercing through the abdominal wall, and an insufflation passage extending along a longitudinal axis and spaced radially from a longitudinal axis of the trocar mandrel. The trocar mandrel recieves an insufflation needle, which includes a latterally disposed opening for the discharge of the insufflation fluid.

5 Claims, 2 Drawing Sheets

TROCAR SPIKE WITH A POINT

This is a National Phase of PCT/DE97/00838 filed Jul. 2, 1997 and based, in turn, on a German Application DE 19616.609.8 filed Apr. 4, 1996.

FIELD OF THE INVENTION

The invention relates to a trocar mandrel with a tip which permits piercing, of the abdominal wall, and hence an insertion into the abdominal cavity.

Such trocar mandrels, which are occasionally referred to as trocars only, are used, for instance, to create an artificial access through the abdominal wall into the abdominal cavity, which is suitable for laparoscopy.

PRIOR ART

In laparoscopic operations the trocar mandrel is introduced into a trocar shaft, which is sometimes referred to as trocar sleeve or simply trocar only. The trocar mandrel with the surrounding trocar shaft is forced through the abdominal wall. When the insertion is completed the trocar mandrel is drawn out from the trocar shaft so that other instruments such as an endoscope, forceps, scissors and/or similar devices may be inserted into the passage of the trocar shaft.

In certain operation techniques a specific needle is introduced prior to the insertion of the trocar into the abdominal wall, which is used for insufflation of the abdominal cavity with a gas, e.g. $CO_2$ in particular.

One example of such a needle is the needle known as "Veress needle", which has normally a diameter of 2.4 mm. After the "insufflation of the abdominal cavity with an insufflation gas, i.e. following the creation of overpressure of up to 50 Torr, the trocar mandrel with the trocar shaft is introduced through another "puncture" or after withdrawal of the Veress needle through the same puncture. In laparoscopic operations the trocar mandrel has a typical diameter of 10 mm.

During the introduction of the trocar mandrel unintended damage may occur in the abdominal cavity; moreover, it may be that the tip of the trocar mandrel is not properly inserted into the abdominal cavity proper.

In the U.S. Pat. No. 5,407,427, discloses a trocar mandrel with a tip which permits the piercing through the abdominal wall. An insufflation passage is provided in the trocar mandrel, which extends along the direction of the longitudinal axis of the trocar mandrel, with the axis and hence the distal discharge opening of the passage being spaced from the tip by a distance in the direction orthogonal on the longitudinal axis of the mandrel which presents an axially symmetrical design in all other respects.

That known trocar mandrel makes it possible to dispense with the use of a Veress needle (cf. the passage from line 51 onwards in column 9 of the U.S. Pat. No. 5,407,427).

There is the disadvantage, however, that while the abdominal wall is pierced the situation may occur that the discharge opening is "clogged" with tissue so that it is no longer—or only insufficiently—possible to insufflate a cavity such as the abdominal cavity.

BRIEF DESCRIPTION OF THE INVENTION

The present invention is based on the problem of improving a trocar mandrel as shown by the U.S. Pat. No. 5,407,427 in such a way that the occurrence of complications, especially as a result of clogging of the insufflation passage in the trocar mandrel, will be prevented whilst it is still possible to dispense with the use of a Veress needle during insertion of the trocar.

In accordance with the present invention in insufflation needle is arranged for displacement in the insufflation passage, which needle comprises a laterally disposed opening for the discharge of the insufflation fluid.

The inventive trocar mandrel can be used in the common manner to create a direct access, e.g. into the abdominal cavity, with the occurrence of complications being precluded which may result from an inappropriate insertion procedure or a lesion caused by the insufflation needle. The arrangement of the discharge opening for the insufflation fluid and particularly the gas on the side of the insufflation needle reliably prevents the clogging of the discharge opening and hence the insufflation access with tissue when the abdominal wall is pierced through. This provision ensures that the insufflation process may be started in a trouble-free manner immediately after the piercing of the abdominal wall.

In an improvement the distal end of the insufflation needle is pointless. On account of the pointless configuration of the distal end of the insufflation needle it is not possible that a tip existing on the insufflation needle will provoke lesions in the abdominal cavity after the abdominal wall has been pierced through.

In any case, the trocar mandrel is still suitable for use in the common manner due to the offset arrangement of the tip and the passage.

The inventive instrument, which combines an insufflation needle such as a Veress needle with a trocar mandrel in one and the same instrument, permits the creation of a direct access to the abdominal cavity so that the undesirable incidences or complications, which may occur when the instruments are used separately, can no longer occur and are at least reduced if not completely avoided.

In the further improvement the distal end of the insufflation needle projects beyond the tip of the trocar mandrel in the normal case. As the insufflation needle is supported for displacement in opposition to a resilient force for sliding back behind the tip, the insufflation needle is pushed back behind the "engagement surface" of the mandrel when the abdominal wall is pierced through. As a result not only an easy piercing through the abdominal wall is ensured but the needle is also protected from damage etc.

The trocar mandrel may present the external shape of a trocar mandrel known per se and may present a conically scarfed tip in particular. In another preferred embodiment the tip may present at least two slopes which form cutting edges. In this design the discharge opening of the insufflation passage may be provided in one of the slopes.

On account of the inventive combination of a Veress needle and a trocar in a single instrument it is moreover possible that the diameter of the insufflation passage and hence of the insufflation needle is larger than the diameter of bore of conventional Veress needles. In particular, the diameter may be roughly 3 mm and more.

It is yet possible to provide (at least) one additional flushing passage in the trocar mandrel for the supply and/or evacuation of a wash fluid, such as a liquid.

The inventive trocar mandrel may, of course, be designed as a disposable trocar. It is preferred, however, that it is suitable for sterilisation for multiple application, and in particular it is configured for being dismantled for sterilisation. This dismantling ensures that cavities etc. can be reliably sterilised, too.

BRIEF DESCRIPTION OF THE DRAWING

The following is an exemplary description of the invention with reference to embodiments, without any restriction of the general inventive idea, and with reference to the drawing which is referred to explicitly, by the way, with respect to the disclosure of all inventive details which are not explained completely in the text. In the drawing.

DESCRIPTION OF AN EMBODIMENT

Figure 1:
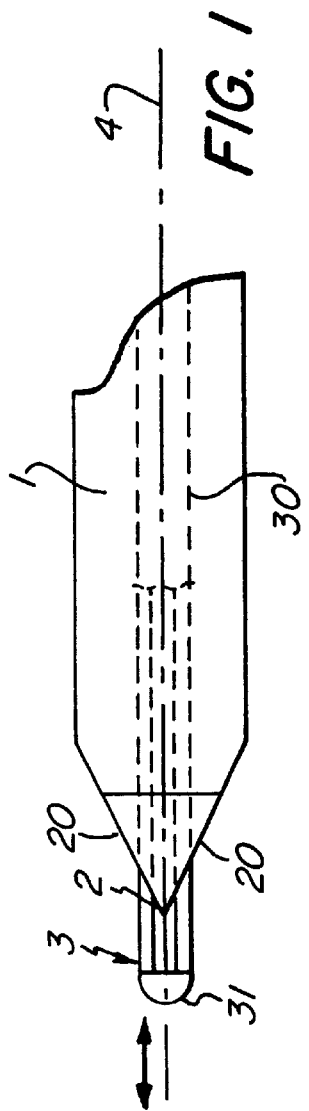
FIG. 1 is a plan view of an inventive trocar mandrel.
Figure 2:
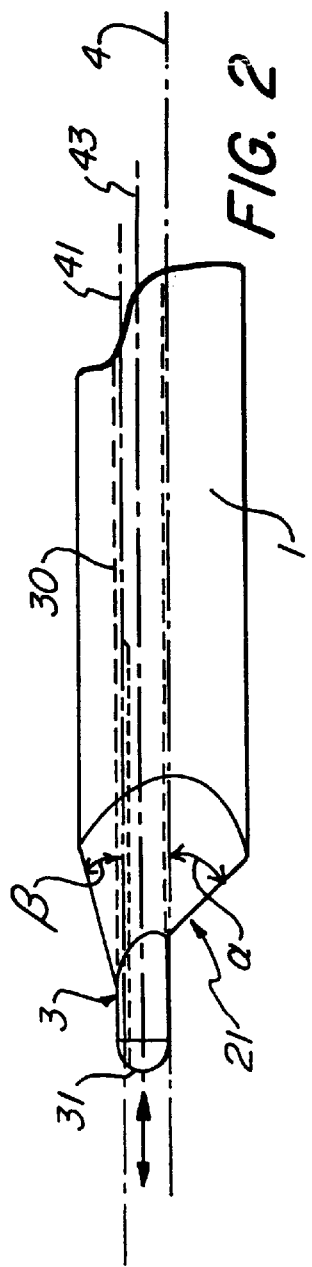
FIG. 2 is a side view.
Figure 3:
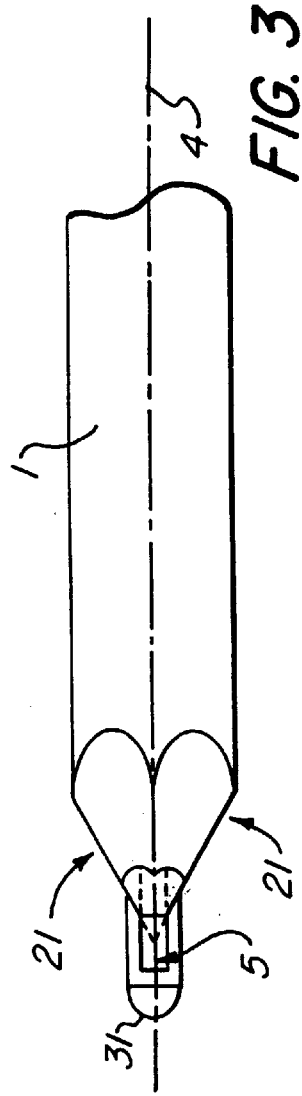
FIG. 3 is a view of the trocar mandrel from below, which is illustrated in FIG. 1.
Figure 4:
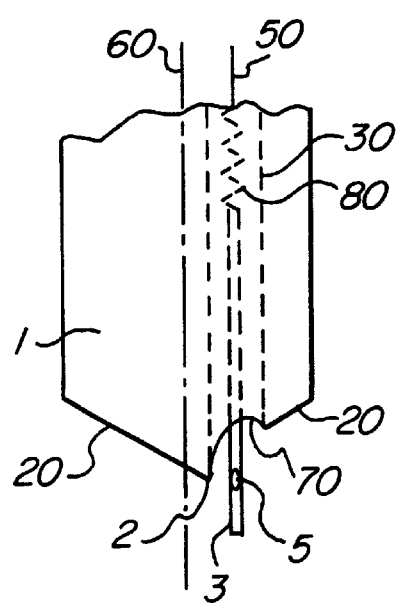
FIG. 4 is a diagrammatic view of a trocar mandrel according to the invention.

An inventive trocar mandrel 1 is illustrated in various views in FIGS. 1 to 3.

The trocar mandrel 1 has a conically scarfed tip 2. In the embodiment illustrated here the tip is formed by two slopes 20 which form cutting edges 21.

An insufflation passage 30 is provided in the inventive instrument, which has a longitudinal axis 43 which is offset relative to the axis 41 passing through the tip of the trocar mandrel, which means that it represents a distance orthogonal on the respective axes.

In the illustrated embodiment moreover both the tip 2 and the insufflation passage 30 are disposed in an off-axis position relative to the center axis 4 of the trocar mandrel so that the trocar mandrel does not have an axially symmetrical basic shape. This may be clearly seen in the side view illustrated in FIG. 2. As shown, one cutting edge extending from tip 2 at angle α is asymmetrical to another cutting edge extending from tip 2 at angle β. As a result the insufflation efficiency is increased—without any impairment when the abdominal wall is pierced through—and the arrangement of the insufflation passage and further ducts if facilitated. It is possible, in particular, to arrange the insufflation passage in the geometric center axis of the trocar mandrel.

The insufflation passage 30 ends, on the distal side, in a recess or a discharge opening 70, or, in the conical (distal) part of the trocar mandrel 1. In a preferred embodiment the insufflation passage 30 is a continuous duct so that an "insufflation needle" 3, which is of the Veress type in particular, can be inserted into this passage from the proximal side, without dismantling the instrument.

A resilient force, which is applied, for instance, by a spring, biases the insufflation needle 3 in such a way that it projects beyond the surface of the slope in which the discharge opening is located, and particularly also beyond the tip 2 of the trocar mandrel 1 in a direction along the axis 4. Under an externally applied force, as it may be created when the abdominal wall is pierced through, the insufflation needle 3 is pushed back behind the surface of the corresponding slope. This is indicated by a double arrow in FIGS. 1 and 2.

Moreover, the distal end 31 of the needle 3 is pointless. As a result, the insufflation needle cannot cause damage on organs, blood vessels, etc., neither in the advanced "basic state" nor in the retracted "introduction state".

Figure 5:
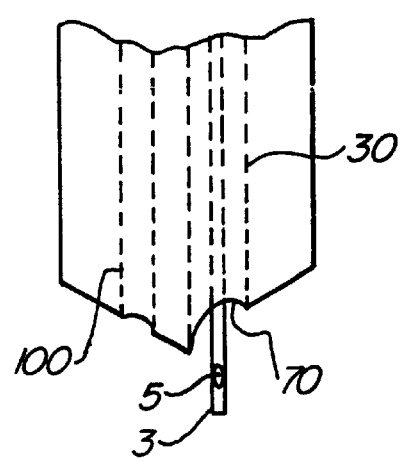
FIG. 5 is a diagrammatic view of a trocar mandrel provided with flushing and insufflation ducts.

A duct which is illustrated in dashed lines—in FIGS. 1 and 2 and shown diagrammatically in FIG. 5—is provided in the needle 3, which serves to pass $CO_2$, for instance, from the proximal end of the instrument to the distal end. This passage ends in an opening 5 through which the insufflation gas is discharged. In accordance with the invention the opening 5 is provided on a lateral surface of the insufflation needle 3 rather than at the face of the needle 3. Due to this arrangement the opening 5 is protected and cannot be clogged with tissue fragments etc. when the abdominal wall is pierced through.

The diameter of bore of the needle 3 is preferably larger than the diameter of the bore in standard needles, e.g. conventional Veress needles.

Moreover, provisions may be made for flushing and sterilisation. To this end, at least one additional duct 100 may be provided through which a wash fluid is supplied or evacuated. Supply and evacuation may also take place in alternation.

In the illustrated embodiment the trocar (or the trocar mandrel, respectively) 1 has a diameter of 10 mm. The insufflation needle 3 has a diameter of 3 mm.

The aforedescribed spring system, which is not shown in the Figures, permits the retraction of the needle 3 behind the slope 20 as soon as the trocar mandrel 1 is supported on the abdominal wall, initially by the pointless tip 31 of the needle 3 and then by the corresponding slope 20. As a result, the tip 2 of the trocar mandrel 1 is released which then pierces through the abdominal wall under the pressure exerted by the operating surgeon. As soon as the abdominal wall has been pierced the insufflation needle 3 returns into its advanced position which is shown in the Figures.

In this state, insufflation takes place. During this operation the trocar scarfed tip 2 is "covered" by the needle 3. The pointless end of the needle 3 hence provides for protection from lesions in the abdominal cavity by the tip 2.

With the tip of the insufflation needle being "pointless", i.e. not sharp-edged, any aggression, i.e. any risk, is avoided in the abdominal cavity.

In a typical laparoscopy the umbilical incision is placed with a linear extension, in depth, in the position from 6 to 12 hours. The abdominal wall is lifted on either side of the navel, with the skin being tightly seized, and under the navel in a way that an angle of roughly 45° relative to the horizontal is produced.

The trocar mandrel is connected to the insufflator which is operated at a low rate, i.e. at a typical efficiency of 1 to 2 liters of gas per minute.

When the trocar mandrel 1 has been inserted into a trocar shaft, which is not shown in the drawing, it is introduced and inserted into the umbilical incision:

The pointless tip of the needle 3 is retracted, the tip 2 at the slope of the trocar mandrel 1 passes transversely through the aponeurosis of the straight muscles and subsequently passes through the peritoneum which presents a lower resistance so that the pointless mandrel can perform its protective function.

At the same time the gas—e.g. $CO_2$—flows into the abdominal cavity and eliminates the virtual vacuum between the two serous membranes: an "air bubble" is created for safety reasons which prevents any collapse of the structures therebelow.

The progress of the operation can be monitored on the pressure gauge means on the insufflator:

An initial overpressure is follows by a negative pressure as soon as the pointless tip 31 of the needle 3 is inside the peritoneal cavity.

It is thus possible for the operating surgeon to detect the progress of the procedure of introduction of the trocar mandrel with the surrounding trocar sleeve with a high degree of reliability.

Then the trocar mandrel is advanced by another 1 to 2 cm so that the shaft will be correctly pushed on. Then the endoscopic operation proper may commence.

The inventive trocar mandrel, which is also referred to as direct trocar or "pneumo trocar", implements the possibility of combining the insufflation function of a Veress needle with the trocar function in one and the same trocar instrument so as to require only a single manual operation. This ensures an improved safety for the patient specifically in view of the acute and sharp trocar tip:

In particular, the inventive configuration ensures an excellent protection from lesion on vessels or any other damage as a result of the potential danger of the tip after its passage through the abdominal wall. The inventive trocar mandrel entails the further advantage that two operations or movements of the hand are combined in a single operation; moreover, the high speed with which the introducing operation can be performed and the simplified monitoring via the pressure gauge means on the insufflator present further advantages. Furthermore, complications are distinctly reduced unless the trocar will be used on a cicatrised abdomen.

The invention has been described in the foregoing with reference to an embodiment, without any restriction of the general feasibility. In particular, the inventive trocar can also be used for operations other than laparoscopy. If necessary, a liquid may equally passed through the passage in the needle, rather than the fluid.

The lateral arrangement of the gas discharge opening 5 entails the advantage that the dischage opening is protected when the instrument is pierced through tissue. At the same time, in the retracted state, the gas flow is practically stopped. When the insufflation needle is advanced, which may be the case in particular under the force of a spring, the insufflation begins automatically without the surgeon being required to start the insufflation procedure separately.

What is claimed is:

1. A trocar assembly for delivering insufflation fluid into a bodily cavity, comprising:

a trocar mandrel extending along a longitudinal center axis and having a distal end;

a cutting tip extending from the distal end and having a pointed end lying in a plane which is spaced radially from the center axis;

an insufflation passage extending along and centered on a longitudinal passage axis and opening into the tip, the passage axis being spaced radially from the pointed end of the cutting tip and from the center axis; and a hollow insufflation needle displaceable in said insufflation passage and having a distal tip formed with a discharge opening located on a lateral surface of said insufflation needle.

2. The trocar assembly defined in claim 1 wherein the distal tip of the insufflation needle is pointless.

3. The trocar assembly defined in claim 1 wherein the cutting tip has at least two slopes formed with cutting edges, said insufflation passage terminating in one of the slopes.

4. The trocar assembly defined in claim 1 wherein said insufflation needle has a diameter approximately equal 3 mm.

5. A trocar assembly for delivering insufflation fluid into a bodily cavity, comprising:

a trocar mandrel extending along a longitudinal center axis and having a distal end;

a tip extending from the distal end and having at least two slopes converging toward one another to form a pointed end lying in an end plane which is radially offset from the center axis, two slopes extending at different angles with respect to the center axis to have at least two cutting edges between the distal end of the trocar mandrel and the pointed end of the tip;

an insufflation passage centered along a passage axis which extends parallel to and is spaced radially from the center axis and from the end plane, said insufflation passage opening into one of the two slopes;

a hollow insufflation needle displaceably mounted in and substantially coaxial with said insufflation passage and having a distal region formed with a discharge aperture oriented in a radial direction relative to the center axis; and a flushing passage internal to said trocar mandrel and proximately located to said insufflation passage for flushing debris from said insufflation passage.

* * * * *